United States Patent
Dogwiler et al.

(10) Patent No.: US 8,403,914 B2
(45) Date of Patent: *Mar. 26, 2013

(54) MEDICAL DEVICE WITH AN ENERGY SUPPLY CARRYING A RESERVOIR

(75) Inventors: Joerg Dogwiler, Bergdietikon (CH); Heiner Kaufmann, Bern (CH); Urs Kipfer, Luetzelfueh-Goldbach (CH); Reto Sigrist, Golaten (CH)

(73) Assignee: Roche Diagnostics International AG, Rotkreuz (CH)

( * ) Notice: Subject to any disclaimer, the term of this patent is extended or adjusted under 35 U.S.C. 154(b) by 247 days.

This patent is subject to a terminal disclaimer.

(21) Appl. No.: 12/878,071

(22) Filed: Sep. 9, 2010

(65) Prior Publication Data
US 2011/0060282 A1    Mar. 10, 2011

Related U.S. Application Data

(63) Continuation of application No. PCT/EP2009/001597, filed on Mar. 6, 2009.

(30) Foreign Application Priority Data

Mar. 10, 2008 (EP) .................................. 08004343

(51) Int. Cl.
*A61K 9/22* (2006.01)
(52) U.S. Cl. .................................................. 604/890.1
(58) Field of Classification Search ............... 604/890.1; 320/116–132
See application file for complete search history.

(56) References Cited

U.S. PATENT DOCUMENTS

| | | | |
|---|---|---|---|
| 3,789,854 A | 2/1974 | Lee | |
| 4,952,862 A | 8/1990 | Biagetti et al. | |
| 5,321,392 A | 6/1994 | Skakoon et al. | |
| 5,825,155 A | 10/1998 | Ito et al. | |
| 6,137,261 A * | 10/2000 | Kurle et al. | 320/132 |
| 6,749,587 B2 * | 6/2004 | Flaherty | 604/151 |
| 7,075,306 B2 * | 7/2006 | Emori et al. | 324/430 |
| 7,598,706 B2 * | 10/2009 | Koski et al. | 320/117 |
| 7,981,102 B2 * | 7/2011 | Patel et al. | 604/500 |
| 8,032,226 B2 * | 10/2011 | Miller et al. | 607/59 |
| 8,125,188 B2 * | 2/2012 | Doll et al. | 320/134 |
| 2003/0160588 A1 * | 8/2003 | Kroll | 320/103 |
| 2005/0248313 A1 * | 11/2005 | Thorland | 320/130 |
| 2007/0093786 A1 * | 4/2007 | Goldsmith et al. | 604/890.1 |

FOREIGN PATENT DOCUMENTS

| | | |
|---|---|---|
| CH | 648936 A5 | 4/1985 |
| CH | 680691 A5 | 10/1992 |
| DE | 3621846 A1 | 1/1988 |
| DE | 3834001 A1 | 4/1990 |
| DE | 19809483 A1 | 9/1999 |

(Continued)

OTHER PUBLICATIONS

International Search Report, Jul. 31, 2009 for International Application No. EP 2009/001597, pp. 1-4.

(Continued)

*Primary Examiner* — Nicholas Lucchesi
*Assistant Examiner* — Diva K Chander
(74) *Attorney, Agent, or Firm* — Dinsmore & Shohl LLP

(57) ABSTRACT

According to one embodiment, a medical device may include an energy supply. The energy supply includes at least two battery stacks, a control unit and a reservoir. The at least two battery stacks include a backup energy source. The control unit may monitor and control the energy supply such that when the control unit detects a fault in the at least two battery stacks, the control unit disconnects a faulty battery stack. The reservoir may be carried by the energy supply.

20 Claims, 7 Drawing Sheets

FOREIGN PATENT DOCUMENTS

| | | |
|---|---|---|
| EP | 0458232 A2 | 11/1991 |
| EP | 0641058 A1 | 3/1995 |
| EP | 0 982 830 A2 | 3/2000 |
| WO | 97/13310 A1 | 4/1997 |
| WO | 00/52807 A1 | 9/2000 |
| WO | 01/21234 A1 | 3/2001 |
| WO | 2004/067066 A1 | 8/2004 |
| WO | 2007/129317 A1 | 11/2007 |

OTHER PUBLICATIONS

US Office Action dated May 21, 2012 relating to U.S. Appl. No. 12/878,074.

Non-Final Office Action pertaining to U.S. Appl. No. 12/878,074, dated May 21, 2012.

* cited by examiner

MEDICAL DEVICE WITH AN ENERGY SUPPLY CARRYING A RESERVOIR

CROSS REFERENCE TO RELATED APPLICATIONS

This application is a continuation of International Application No. PCT/EP2009/001597 filed Mar. 6, 2009 which claims priority to European Patent Application No. EP08004343.3 filed on Mar. 10, 2008, both of which are herein incorporated by reference in their entirety.

The present application is related to U.S. patent application Ser. No. 12/878,074 filed Sep. 9, 2010, and entitled "MEDICAL DEVICE WITH AN ENERGY SUPPLY HAVING AT LEAST TWO ENERGY SOURCES" which is herein incorporated by reference in its entirety.

TECHNICAL FIELD

The present disclosure relates to medical devices and medical systems. In particular, the embodiments described herein relate to medical devices and medical systems for diabetes treatment comprising a reservoir.

BACKGROUND

Portable medical devices may be powered by non-rechargeable batteries.

For example, WO 2000/52807 A1, which is incorporated by reference herein, discloses a battery pack circuit comprising a plurality of battery cells, each of them constituting an energy source. Depleted battery cells can be switched with charged battery cells via a battery switching circuit when the monitored voltage falls below a predetermined level.

EP 0982830 A2, which is incorporated by reference herein, discloses a battery pack with a plurality of cells which are, together with a protective circuit, encased in a container. The protective circuit comprises a cell failure detector for each of the cells and a cell interrupter to disconnect a faulty cell.

Accordingly, additional medical devices and medical systems comprising an energy supply and a reservoir with a reduced failure rate are desired.

SUMMARY

According to one embodiment, a medical device may include an energy supply. The energy supply includes at least two battery stacks, a control unit and a reservoir. The at least two battery stacks include a backup energy source. The control unit may monitor and control the energy supply such that when the control unit detects a fault in the at least two battery stacks, the control unit disconnects a faulty battery stack. The reservoir may be carried by the energy supply.

According to another embodiment, a medical system may include a medical device including an energy supply and a charging station for charging the energy supply. The energy supply includes at least two battery stacks, a control unit and a reservoir. The at least two battery stacks include a backup energy source. The control unit may monitor and control the energy supply such that when the control unit detects a fault in the at least two battery stacks, the control unit disconnects a faulty battery stack. The reservoir may be carried by the energy supply. The charging station includes an USB-plug, a line connector, a solar cell panel, a primary battery, a plug for a car cigarette lighter outlet, a connector for a mobile phone accumulator, a dynamo, or a combination thereof for supplying energy.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
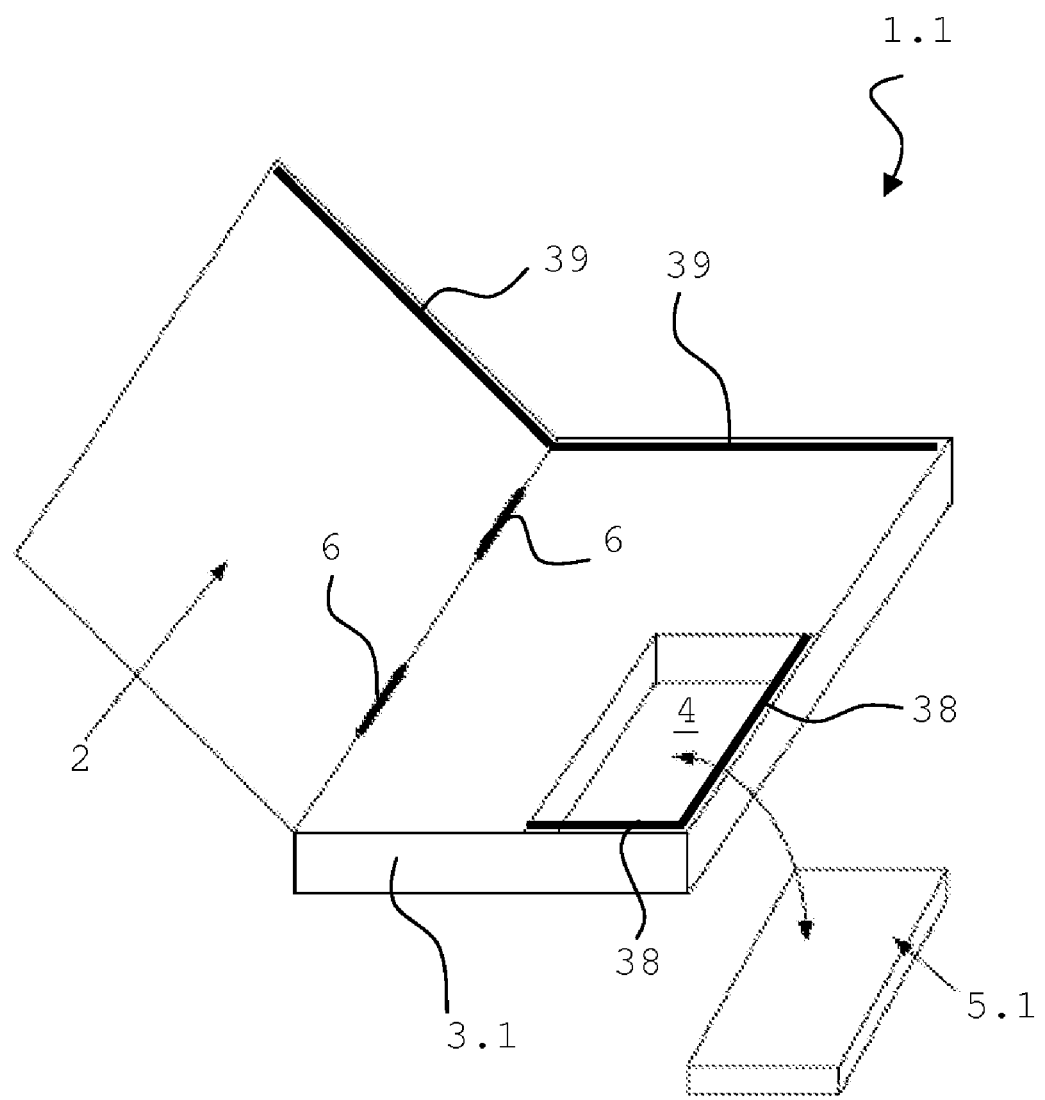
FIG. 1 schematically depicts a medical device according to one or more of the embodiments shown and described herein.

According to the embodiments described herein, a medical device comprising an energy supply and a control unit for monitoring and controlling the energy supply is provided. The energy supply may comprise at least two energy sources. The at least two energy sources comprise a backup energy source. The backup energy source may be used for supplying energy in cases where no backup is needed for the other of the at least two energy sources. The control unit can detect a fault in the energy sources and can disconnect the faulty energy source upon fault detection.

Therefore, the embodiments described herein may operate as a redundant system that can be colloquially termed "fail-safe" or "single fault safe." For example, if one of the energy sources fails then one of the other energy sources functions as a backup energy source. The backup energy source may take over the function of the faulty energy source or provide enough energy to serve as an emergency energy supply for triggering an alarm. Thus, fail-safe operation of the medical device is provided even if a fault occurs in one of the energy sources of the energy supply.

In one embodiment, the control unit comprises means for measuring and evaluating the output voltage and/or current of each energy source and means for disconnecting each energy source from the rest of the medical device, i.e. the load of the energy supply. For example, the control unit may comprise a control subunit for each energy source. Each control subunit comprises means for measuring and evaluating the output voltage and/or current of an associated energy source and means for disconnecting the associated energy source from the load. For a medical device such as an insulin pump, the load is the pump.

In another embodiment the energy supply is rechargeable and comprises a lithium-ion polymer battery with at least two of the battery stacks. Lithium-ion polymer batteries are also commonly referred to as lithium polymer batteries or polymer lithium ion batteries. However, for convenience the term lithium-ion polymer battery is used herein rather than listing all of the nomenclatures for such batteries and their equivalents. Each battery stack operates as one energy source and comprises a terminal or contact of positive potential and a terminal or contact of negative potential. Each battery stack may furthermore comprise one or more battery cells such as, for example, one or more battery bi-cells. As used herein the term "bi-cell" means a cell with one anode and two cathodes, the cathodes being positioned on either sides of the anode. The height of a bi-cell may be, for example, in the range of 600 to 800 micrometers.

Lithium-ion polymer batteries may be robust to physical damage and can be cost-efficiently manufactured. Furthermore, lithium-ion polymer batteries may be rechargeable, i.e. once the original energy supply has been discharged the energy supply may be substantially restored. The energy provided by a lithium-ion polymer battery per volume is relatively high, which may broaden application and/or device integration possibilities and possibly prolong running time. Due to their polymeric nature, lithium-ion polymer batteries do not require a rigid casing and can be specifically shaped to fit into a space such as within a medical device. Specifically, a lithium-ion battery can be shaped to match and substantially fill a space provided by a medical device for an energy source. Therefore, for a given shape, a relatively high energy source capacity can be provided. Furthermore, lithium-ion polymer batteries can be manufactured to be relatively thin to correspond to a relatively thin medical device configured to be discreetly employed or used by a user such as an insulin pump. Further, since lithium-ion polymer batteries have a relatively low gravimetric density, the weight of the medical device can be reduced, leading to an easier-to-carry medical device. Also due to their relatively high volumetric density, lithium-ion polymer batteries may provide a relatively long running time for the energy supply of the medical device. Lithium-ion polymer batteries have a relatively small internal resistance and are generally robust, i.e. tolerant, with respect to temperature and power variations. Since the cell-voltage and the discharge voltage range (typically 4.2 Volt-3.0 Volt) of a lithium-ion polymer battery are relatively high, the energy supply and the energy source, respectively, have relatively low susceptibility to contamination of their terminals or contacts.

In the embodiments described herein, a reservoir is provided that is carried by the energy supply. As used herein, the term "reservoir" refers to a fluid reservoir for storing a liquid drug, such as an insulin formulation.

By combining the reservoir for fluid and the energy supply in one unit, the therapeutic handling operation of reservoir refill or exchange and the technical handling operation of energy supply exchange or recharge may be combined into one operation. Furthermore, the interfaces for fluid and for electric energy may also be combined in this one unit for sealing purposes.

Medical systems are provided by the embodiments described herein, the medical system comprising a medical device as described herein and a charging station for an energy supply of a medical device as described herein.

In one embodiment, the charging station comprises an energy supplying means such as, for example, an USB-plug, a line connector (also called network connector), a solar cell panel, a primary battery, a plug for a car cigarette lighter outlet, a connector for a mobile phone accumulator, a dynamo with a crank handle, or a combination thereof. For example, a charging station may comprise at least two different energy supplying means. By providing several different types of energy supplying means, the charging station is not restricted to one type of energy (e.g. a primary battery) but can switch to a different kind of energy, in particular to a different kind of primary energy, (e.g. solar energy or the energy provided by a car battery via a cigarette lighter outlet) which is available at that moment. The energy switching capability may increase energy independence and reduce cost, while providing a substantially consistent and substantially uninterrupted energy supply. For example, energy may be available in non-everyday situations such as during vacation, during travel or in free time. Hence, charging stations according to the embodiments described herein may enhance user individuality and flexibility. The user can charge the energy supply of his medical device as needed and according to his needs and according to the availability of energy resources. The embodiments described herein may adapt with outer circumstances such as, for example, while in the office the line connector or the USB-plug may be utilized, while on vacation the solar energy may be utilized or the dynamo may be utilized by rotating the crank handle, and so on.

Medical devices comprising a reservoir are provided herein such as, for example, insulin pumps.

According to one embodiment, FIG. 1 schematically depicts a medical device 1.1 comprising a top cover 2. The top cover 2 forms part of the housing 3.1 of the medical device 1.1. The top cover 2 may be mounted pivotally to the housing 3.1 on hinges 6. The medical device 1.1 comprises a compartment 4 for an energy supply 5.1 which is replaceable. The replacement capability of the energy supply 5.1 is generally indicated in FIG. 1 by a bent arrow. As depicted in FIG. 1, the energy supply 5.1 can be placed in the compartment 4 within the housing 3.1 of the medical device 1.1. No specific sealing functions have to be performed between the outer surfaces of the energy supply 5.1 and the compartment 4. Therefore, no specific sealing or gaskets have to be provided at the contact surfaces of the energy supply 5.1 and the compartment 4. The top cover 2 or the housing 3.1 may be sealed. For example, gaskets 39 or other sealing devices may be used to seal the top cover 2 or the housing 3.1. Furthermore, gaskets 38 may be arranged at contact surfaces of the compartment 4 for sealing.

Figure 2:
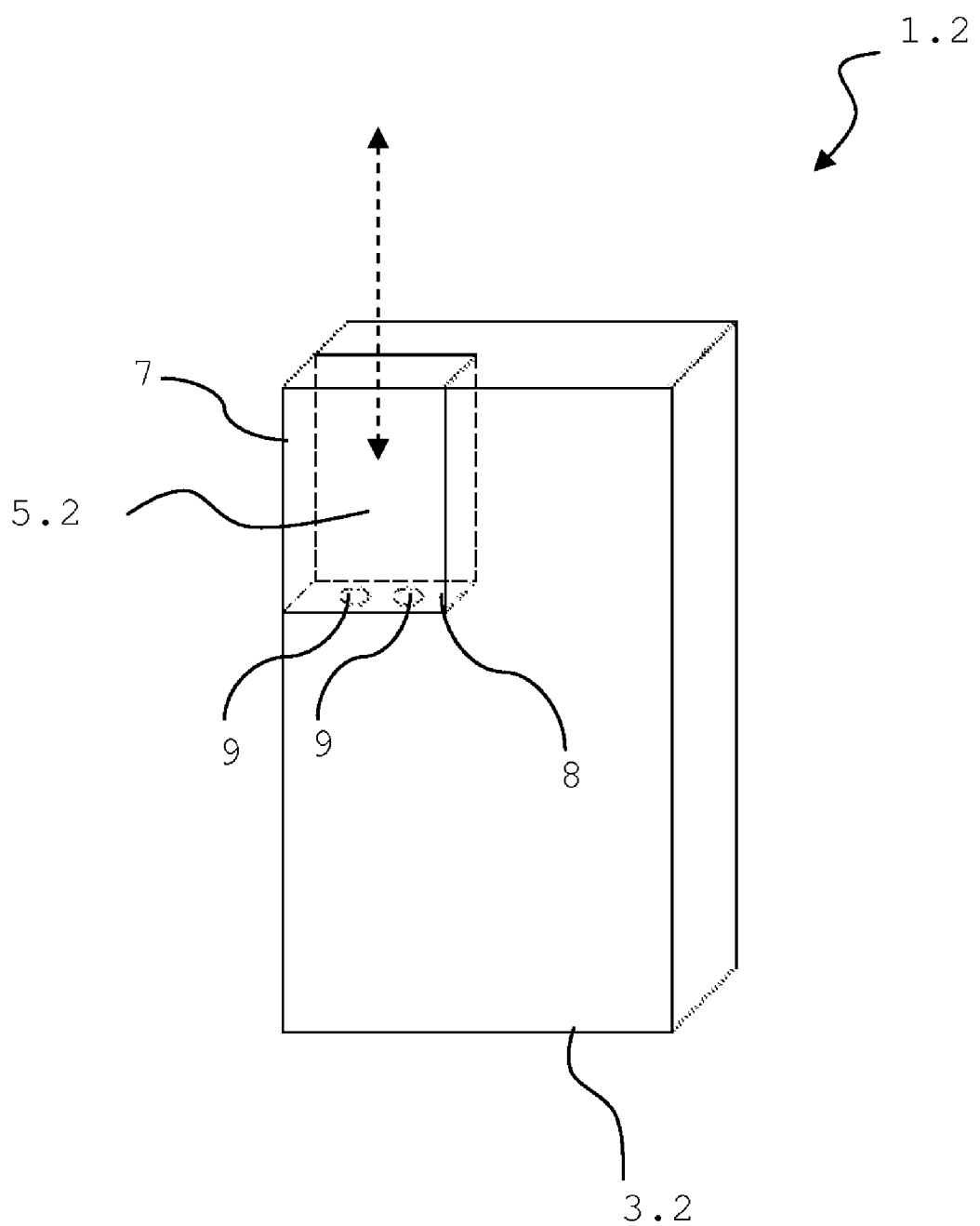
FIG. 2 schematically depicts a medical device according to one or more of the embodiments shown and described herein.

FIG. 2 schematically depicts another embodiment of a medical device 1.2 comprising an energy supply 5.2 that is replaceable. The dashed arrow generally indicates the motion of an energy supply 5.2 as it is exchanged. As depicted in FIG. 2, a portion of the housing 3.2 of the medical device 1.2 is formed by an energy supply housing 7 for the energy supply 5.2. The energy supply 5.2 comprises terminals 9 (or contacts) and a contact surface 8 that forms an outer surface with the terminals 9. For sealing purposes, the contact surface 8 may be provided with a sealing device, such as, for example, one or more gaskets. The sealing device may protect the medical device 1.2 against humidity, i.e., by sealing the terminals 9. While only two of the terminals 9 are depicted in FIG. 2, it is noted that the energy supply 5.2 may comprise any number of terminals. Furthermore, it is noted that the embodiments described herein may be sealed such the medical device 1.2 conforms to IPX8 (international protection rating X8), i.e. the medical device 1.2 is protected against harmful ingress of water up to and beyond 1 meter. Thus, the medical device 1.2 may be suitable for continuous immersion in water under conditions which shall be specified by the manufacturer as described at the following URL http://en.wikipedia.org/wiki/IP_Code, which is incorporated by reference herein.

Figure 3:
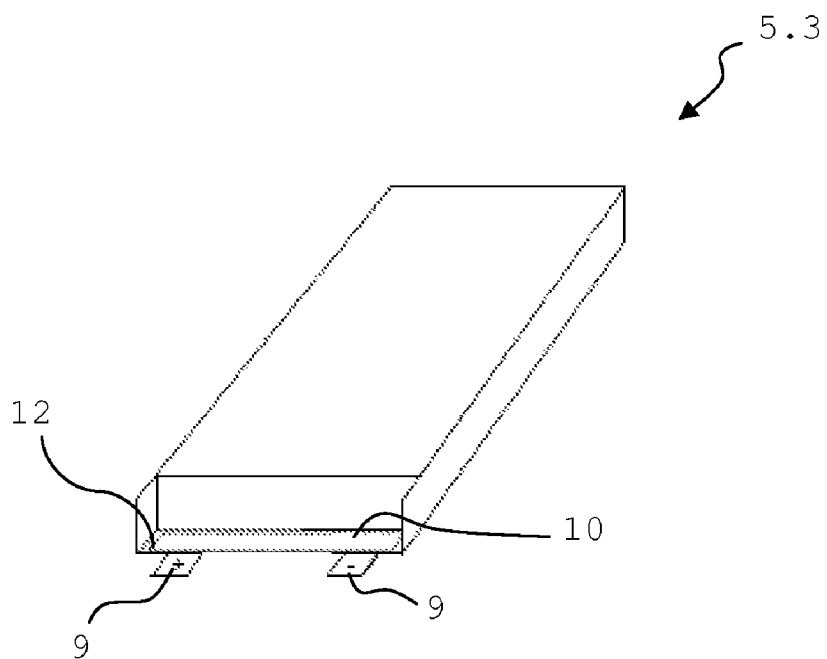
FIG. 3 schematically depicts an energy supply according to one or more of the embodiments shown and described herein.

Referring now to FIG. 3, an energy supply 5.3 according to the embodiments described herein is schematically depicted. The energy supply 5.3 comprises a rechargeable lithium-ion polymer battery with, for example, a nominal cell voltage of 3.7 Volt. The energy supply 5.3 furthermore comprises a fuel gauge unit 10 for estimating and monitoring its remaining running time and/or life time. As used herein the term "fuel" means the charge of the energy supply 5.3 or the energy which can be provided by the energy supply 5.3. The fuel gauge unit 10 determines the remaining running time via energy or impedance measuring. For example, the fuel gauge unit 10 may comprise so-called "smart" electronics.

Due to a laminated design, the lithium-ion polymer battery may consist of several battery cells, in particular bi-cells. Two or more battery stacks, each consisting of battery cells, may be integrated as independent energy sources in one replaceable unit such as the energy supply 5.3. For example, referring collectively to FIGS. 3 and 5 through 8, the lithium-ion polymer battery may comprise two of the battery stacks 11 with each of the battery stacks 11 representing one energy source. Each of the battery stacks 11 has a terminal 9 of positive potential and a terminal 9 of negative potential. Thus, there are therefore four terminals 9 with two of the battery stacks 11. Furthermore, each of the battery stacks 11 is provided with a protection circuit 12 for protection against overcharge, over-voltage, under-voltage, or combinations thereof. There can be provided one of the fuel gauge units 10 for the entire energy supply 5.3 or one of the fuel gauge units 10 allotted to each of the battery stacks 11. The fuel gauge unit 10 and the protection circuit 12 may be enclosed by the energy supply housing 7 (not depicted in FIG. 3) and integrated in the energy supply 5.3.

Figure 4:
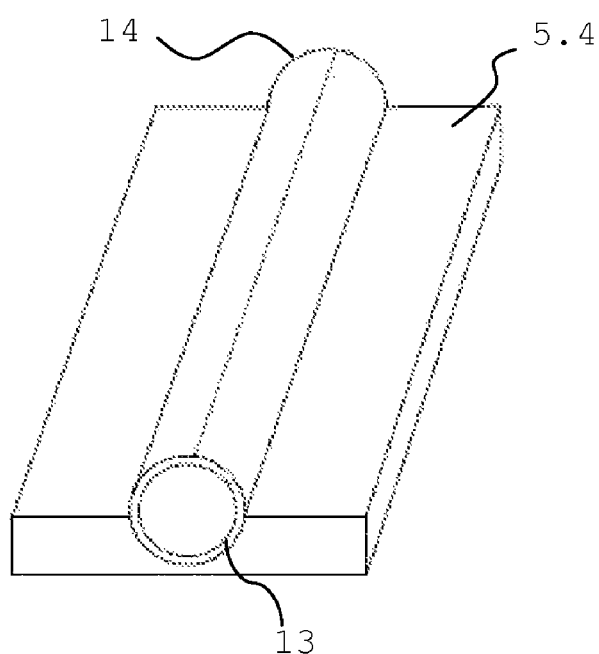
FIG. 4 schematically depicts an energy supply supporting a reservoir for a fluid according to one or more of the embodiments shown and described herein.

Medical devices, according to the embodiments described herein, may comprise a reservoir for a fluid which is carried by an energy supply. For example, a medical device such as an insulin pump typically comprises a reservoir such as a cartridge for insulin. FIG. 4 depicts an energy supply 5.4, according to the embodiments described herein, comprising a cavity 13 for accommodating a reservoir 14. The cavity 13 may be formed to accommodate a reservoir 14 that is cylindrically shaped such as a cartridge of an insulin pump. The reservoir 14 can be formed at least in part by the housing of the energy supply 5.4, e.g., the reservoir may be enclosed by or may be held and supported by the housing of the energy supply 5.4.

In another embodiment, the energy supply 5.4 carries components of a medical device, e.g., if the medical device comprises a glucose meter, one or more glucose test strips or a test strip drum. The energy supply 5.4, the reservoir 14, and other components can be assembled outside the medical device. After assembly, the assembled components can be inserted as one unit into the medical device. For example, the reservoir 14 (e.g., a cartridge), or a bag can be placed in the cavity 13 before the energy supply 5.4 is inserted into the medical device. If the cavity 13 is formed by the housing of the energy supply 5.4, the housing also serves as support for the reservoir 14 in addition to constituting a housing for the energy supply 5.4.

In other embodiments the reservoir (and/or other components of the medical device) may carry and support the energy supply.

In addition to combining the reservoir for fluid and the energy supply comprising fuel gauge unit(s) and protection circuit(s) into one unit, the interfaces for fluid and for electric energy may also combined in the one unit for sealing purposes. In one embodiment, the capacity of the reservoir and the running time of the energy supply are time-synchronized. A change or refill of the reservoir may be substantially coincident in time with a required change or recharge of the energy supply. For example, the remaining running time of the energy supply may be estimated by the fuel gauge unit. Hence, the therapeutic handling operation of reservoir refill or exchange can be combined with the technical handling operation of energy supply exchange or recharge.

FIGS. 5 to 8 depict energy supplies according to the embodiments described herein. The energy supply housing 7 is generally depicted in FIGS. 5 to 8 dashed elliptical for simplicity and not by way of limitation. Although not depicted in FIGS. 5 to 8 as touching, it is noted that the terminals 9 of the battery stacks 11 are connected to corresponding contacts 18 of the energy supply housing 7 (where correspondence is indicated by "+" for positive potential and "−" for negative potential).

Figure 5:
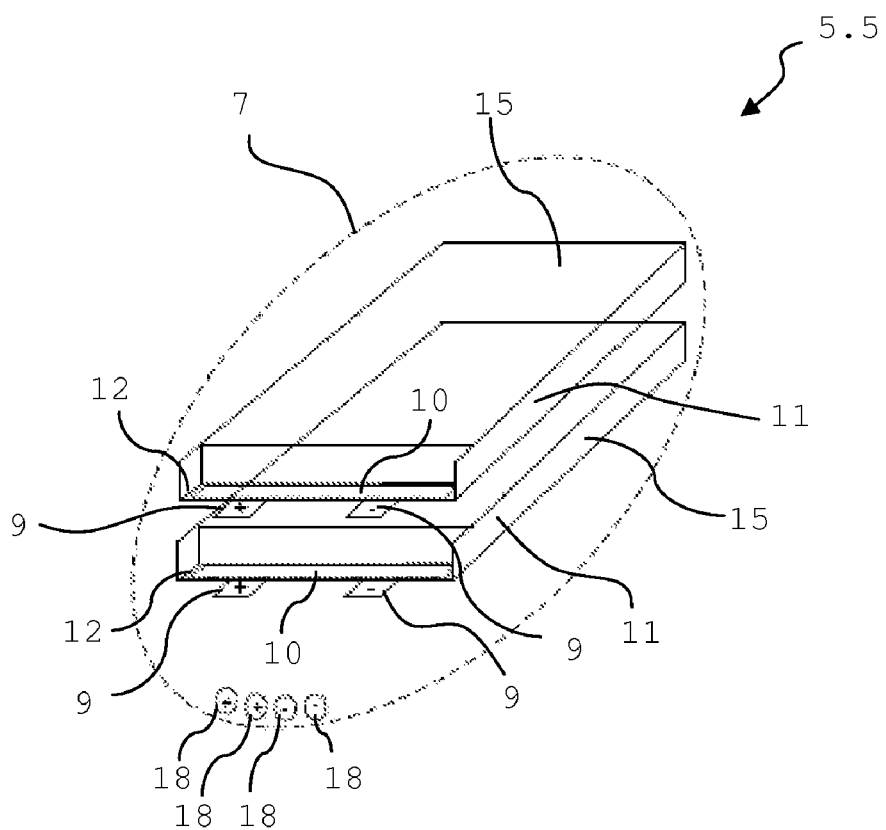
FIG. 5 schematically depicts an energy supply with two energy sources according to one or more of the embodiments shown and described herein.

FIG. 5 depicts an energy supply 5.5 comprising a rechargeable lithium-ion polymer-battery with at least two of the battery stacks 11 as energy sources as described above. Each of the battery stacks 11 comprises a cover 15. The cover 15 may be made of laminated aluminum foil. The battery stacks 11 are placed on top of each other within the energy supply housing 7. The energy supply housing 7 may be made of plastics. In one embodiment, the energy supply 5.5 is fully redundant, i.e., the battery stacks 11 and their covers 15 are equally structured. It is noted that there can be one of the fuel gauge units 10 for the entire energy supply 5.5 or there can be one of the fuel gauge units for each of the battery stacks 11. The fuel gauge unit 10 and the protection circuit 12 may be enclosed by the energy supply housing 7 and integrated in the energy supply 5.5.

Figure 6:
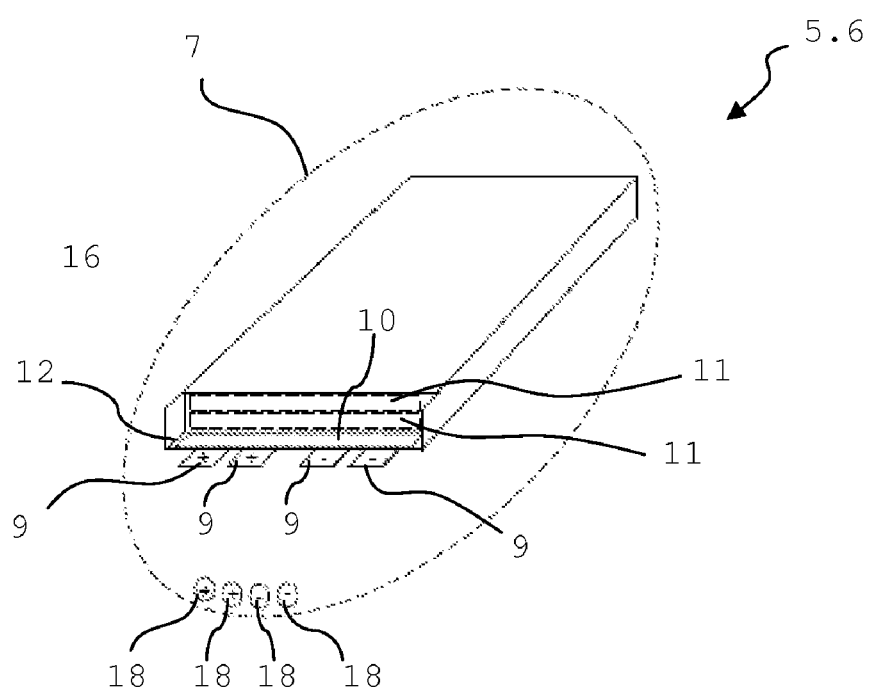
FIG. 6 schematically depicts an energy supply with two energy sources according to one or more of the embodiments shown and described herein.

In another embodiment, schematically depicted in FIG. 6, the energy supply 5.6 comprises two of the battery stacks 11 that are enclosed by one common cover 16, which may be made of laminated aluminum foil. This embodiment may also be referred to as quasi redundant.

Figure 7:
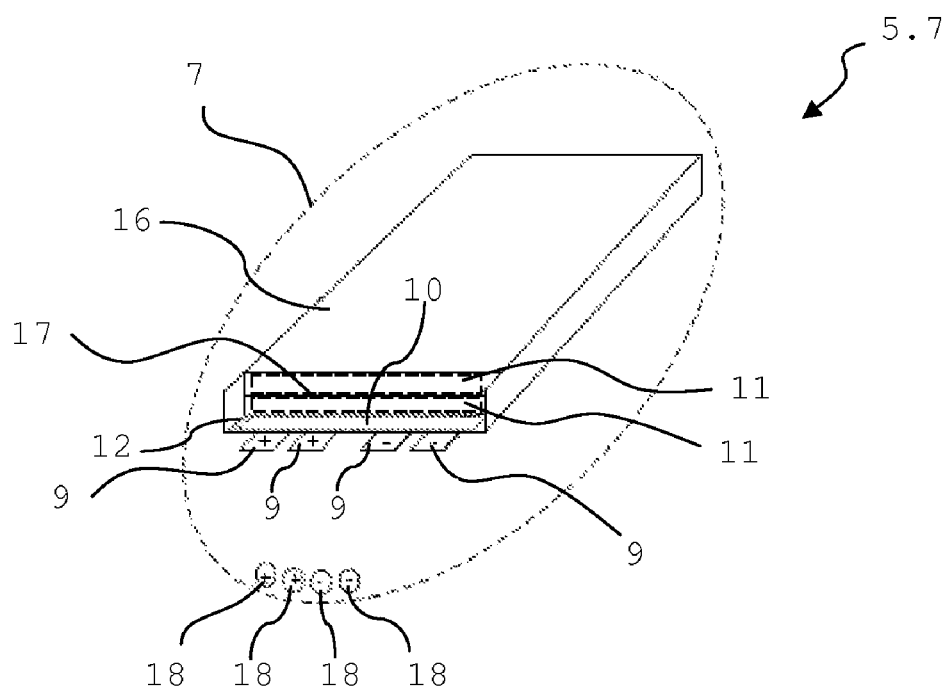
FIG. 7 schematically depicts an energy supply with two energy sources according to one or more of the embodiments shown and described herein.

In a further embodiment, schematically depicted in FIG. 7, the energy supply 5.7 comprises battery stacks 11 that are separated by a sealing sheet 17, which may be made of laminated aluminum foil. This embodiment may also be referred to as quasi redundant. In FIG. 7 the battery stacks 11 are depicted as being separated by one layer (the sealing sheet 17), while in FIG. 5 the battery stacks are depicted as being separated by two layers (twice the cover 15). Therefore, the quasi redundant embodiments, as schematically depicted in FIG. 7, need less space than the fully redundant embodiments, as schematically depicted in FIG. 5.

Figure 8:
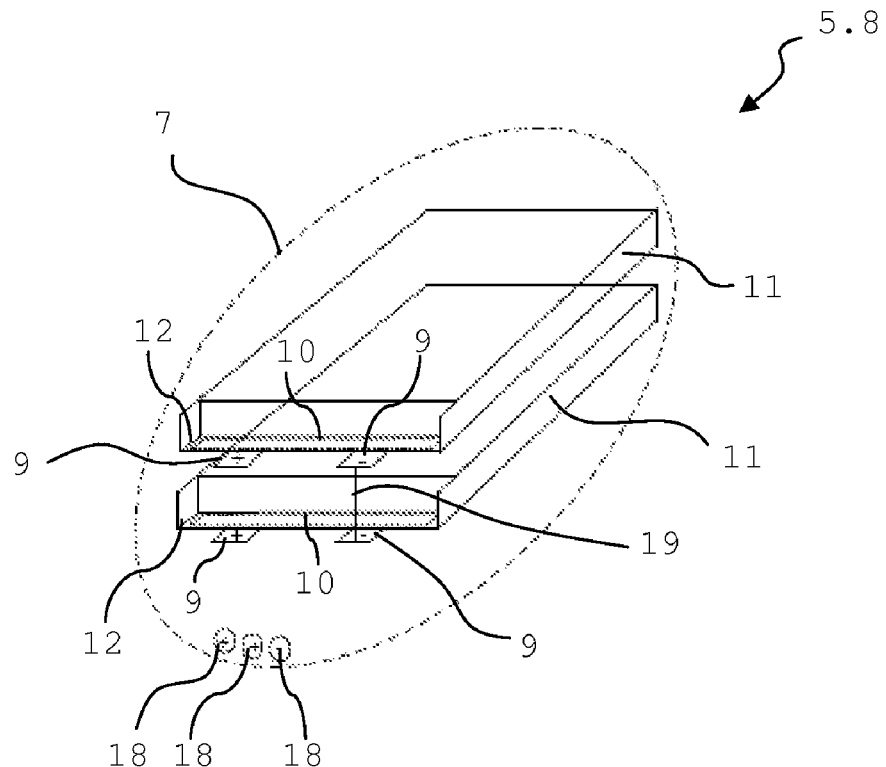
FIG. 8 schematically depicts an energy supply with two energy sources according to one or more of the embodiments shown and described herein.

Referring now to FIG. 8, in one embodiment of the energy supply 5.8, each of the terminals 9 of negative potential of the battery stacks 11 are connected to one common terminal 19 of negative potential. The energy supply housing 7 comprises contacts 18 that correspond and are connected to the terminals 9 of positive potential and to the one common terminal 19 of negative potential. Accordingly, a connection of the terminals 9 of negative potential to form one common terminal 19 of negative potential may be made in any of the embodiments described herein.

It is noted that while the battery stacks 11 are depicted in FIGS. 5 to 8 as being placed on top of one another, the battery stacks 11 can be arranged differently, for example, next to each other. Furthermore, it is noted that any of the features of the depicted energy supplies of FIGS. 1 to 8 may be combined in embodiments having all possible combinations.

Referring collectively to FIGS. 1 to 8, the contacts 18 of the energy supply housing 7 may be connected to the terminals 9 or the common terminal 19 of the battery stacks 11. The contacts 18 represent the electrical interface of the energy supply 5.1 to 5.8. The output voltage and/or current of the contacts 18 may be monitored periodically for the detection of faults of the battery stacks 11, for example, within a multiple error occurrence period. Once a fault is detected, the battery stack 11 having the fault may be switched off, i.e., disconnected, and its function may be taken over by the other of the battery stacks 11. The multiple error occurrence period is defined as the period of time, in which the probability for the occurrence of multiple faults that are safety critical is sufficiently small for a particular requirement class. The multiple error occurrence period starts at the last point in time where the monitored device/system is in a fault-free state according to the considered requirement class. The fault detection in one of the battery stacks 11 may cause switching to a battery stack 11, without a fault, that may ensure safe operation for a time period that is long enough to trigger and/or produce an alarm, for example, an alarm for a given time.

Figure 9:
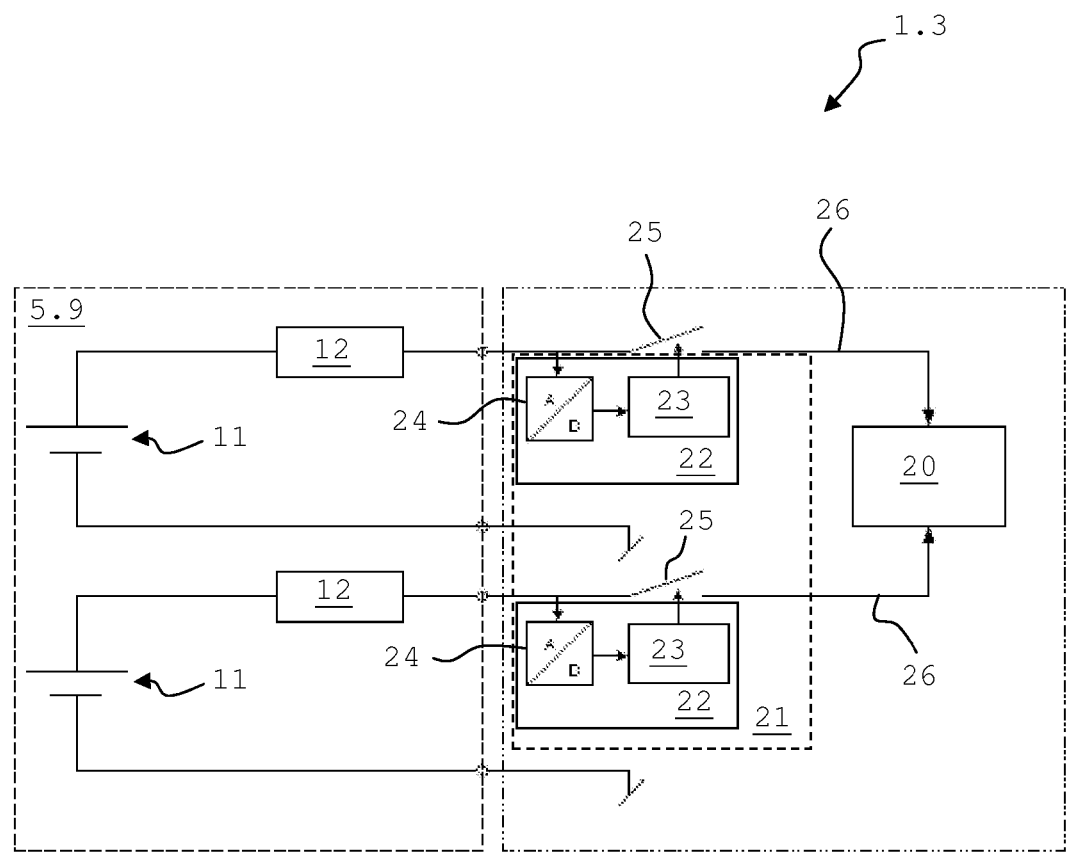
FIG. 9 depicts a block diagram of a medical device according to one or more of the embodiments shown and described herein.

Referring now to FIG. 9, a schematic block diagram of a medical device 1.3 is depicted, according to the embodiments described herein such as, for example, medical device 1.1 (FIG. 1) and medical device 1.2 (FIG. 2). The medical device 1.3 comprises an energy supply 5.9 such as, for example, energy supplies 5.1, 5.2, 5.3, 5.4, 5.5, 5.6, 5.8 (FIGS. 1 to 8). The energy supply 5.9 comprises a rechargeable lithium-ion polymer battery with two of the battery stacks 11. Each of the battery stacks 11 is provided with a protection circuit 12. The energy supply 5.9 supplies energy to a load 20, e.g., a pump in an insulin pump medical device. The load 20 can comprise several sub-loads. A control unit 21 is provided with a control subunit 22 for each of the battery stacks 11. Although the control subunits 22 are depicted in FIG. 9 as integrated in one unit as control unit 21 (generally indicated by the dashed box), the control subunits 22 may be separate units. Each of the control subunits 22 comprises means for measuring and evaluating (not shown in FIG. 9) the output voltage and/or current of the battery stack 11 it is allotted to and a disconnecting means 23 for disconnecting the battery stack 11 from the load 20. The means for measuring and evaluating may comprise an analog sensor for measuring the output voltage and/or current. The analog measurement signal is then converted by an analog-digital converter 24 of the control subunit 22 into a digital signal which can then be evaluated by the disconnecting means 23 or another evaluation circuit. The disconnecting means 23 for disconnecting the battery stack 11 may control a switch 25 in the electrical path 26 from the battery stack 11 to the load 20. The control unit 21 may also comprise the fuel gauge unit(s) 10 (not shown in FIG. 9) and the protection circuit(s) 12, for example, when used with a fix installed lithium-ion polymer battery.

If the means for measuring and evaluating of one of the control subunits 22 detects a fault in the battery stack 11 it is allotted to, then the disconnecting means 23 controls the switch 25 such that it opens and disconnects the electrical path 26 from the battery stack 11 with the fault to the load 20. The battery stack 11 without the fault becomes responsible for supplying electrical energy, for example, for continued operation or alarming. Examples of faults include: a battery stack 11 that provides no output voltage, a battery stack 11 that provide an output voltage below a pre-defined threshold stored in the control unit 21 or the control subunits 22, or a failure of a battery connection.

The energy distribution among the battery stacks 11 may be, for example, 50/50, i.e., each of the battery stacks 11 provides 50 percent of electrical energy required by the load 20. If the load 20 comprises several sub-loads, the sub-loads may be allotted to the battery stacks 11 to maintain the desired energy distribution. Furthermore, the energy distribution among the battery stacks 11 may be different and asymmetric, for example, 95/5, where one of the battery stacks 11 provides 95 percent of the electrical energy and the other of the battery stacks 11 provides 5 percent. A battery stack 11 supplying a low amount of electrical energy (e.g., 5 percent) may serve as an emergency energy supply for triggering an alarm in case of a fault. The electronics (not shown in FIG. 9) of the load 20 may be designed such that it can alternatively access each or both of the battery stacks 11 while determining their respective output voltages.

Figure 10:
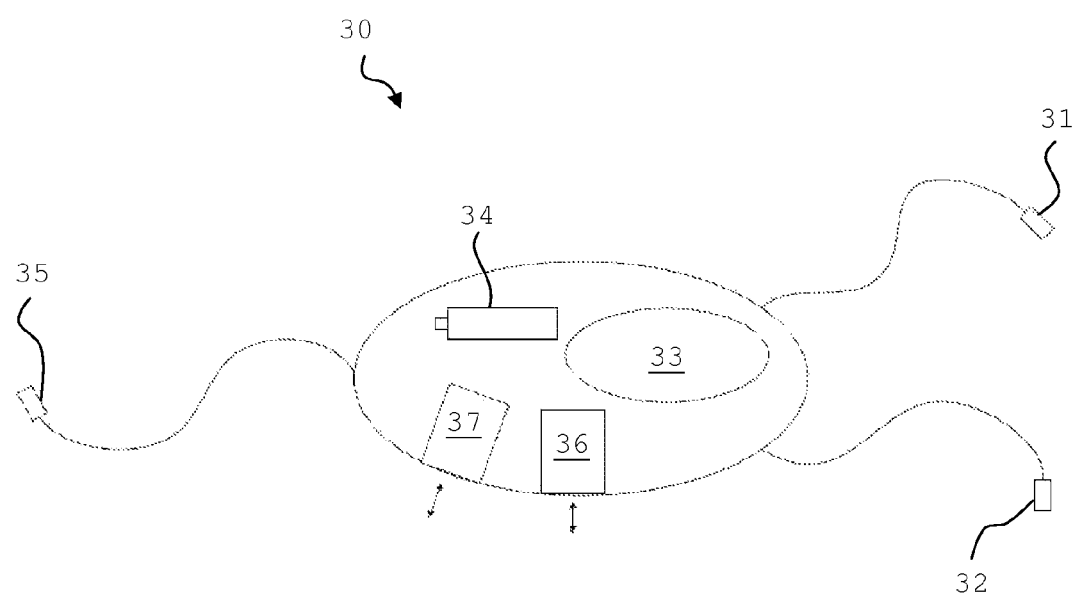
FIG. 10 schematically depicts a charging station of a medical system according to one or more of the embodiments shown and described herein.

Referring now to FIG. 10, a charging station 30 according to the embodiments described herein is schematically depicted. The charging station 30 may be utilized for charging an energy supply 5.1, 5.2, 5.3, 5.4, 5.5, 5.6, 5.7, 5.8, 5.9 (FIGS. 1 through 9) of a medical device 1.1, 1.2, 1.3. For example, the charging station 30 and a medical device 1.1, 1.2, 1.3, as described herein, may be combined to make a medical system. In one embodiment, the charging station 30 comprises an energy supplying means such as, for example, a USB-plug 31, a line connector 32 (e.g., a network connector or a 110-230 VAC/DC plug for supplying 110 to 230 Volts of alternating current to direct current plug), a solar cell panel 33, a primary battery 34 (e.g. an AA battery, an AAA battery and/or a 9 Volt block battery) and a plug 35 for a car cigarette lighter outlet (i.e. an 12 Volts of direct current (VDC) car plug). The charging station 30 comprises a charge slot 36 for the energy supply 5.1, 5.2, 5.3, 5.4, 5.5, 5.6, 5.7, 5.8, 5.9 which is connected or connectable to the USB-plug 31, the line connector 32, the solar cell panel 33, the primary battery 34, the plug 35, or a combination thereof via a charging circuit (not depicted in FIG. 10).

By providing several different types of energy supplying means, the user is not restricted to one type of energy (e.g. a primary battery 34) but can switch to a different type of energy (e.g. solar energy if the solar cell panel 33 is exposed to sunlight or car battery if the charging station is connected with a car) which is available at the particular moment. The capability to switch between different types of energy may enhance the independency of the embodiments described herein from purchasable primary batteries and may increase energy availability in non-everyday situations such as vacation or travel.

The charging station 30 may further comprise a storage slot 37 for storing an energy supply 5.1, 5.2, 5.3, 5.4, 5.5, 5.6, 5.7, 5.8, 5.9 (FIGS. 1 through 9). For example, an energy supply may be stored such that it remains in a desired charge condition, in particular, basically fully charged. The storage slot 37 is connected or connectable to the energy supplying means. An energy supply 5.1, 5.2, 5.3, 5.4, 5.5, 5.6, 5.7, 5.8, 5.9 stored in the storage slot 37 may be kept at its nominal cell voltage (e.g., between about 3.0 and about 3.7 Volts) through charge preservation. The electrical energy required for maintaining the nominal cell voltage is provided by the USB-plug 31, the line connector 32, the solar cell panel 33, the primary battery 34, the plug 35, or a combination thereof of the charging station 30. A control circuit (not depicted in FIG. 10) may cooperate with the storage slot 37 for controlling the charge of the stored energy supply such that its nominal cell voltage does not fall below a voltage (e.g., about 3.0 Volts) and is within range of the desired storage voltage (e.g., about 3.7 Volt). In another embodiment, the nominal cell voltage is maintained in a proper charge condition by the charging circuit. For example, the charging circuit may supervise the voltage of the energy supply 5.1, 5.2, 5.3, 5.4, 5.5, 5.6, 5.7, 5.8, 5.9 after having it charged in order to ensure proper/desired storage condition.

The charging station 30 may further comprise a display (not depicted in FIG. 10) for displaying the actual charge of an energy supply inserted into the charge slot 36 and/or the storage slot 37. Furthermore, the charging station may comprise more than one of the charge slots 36 and/or more than one of the storage slots 37. For example, there may be one display for each of the charge slot 36 and the storage slot 37. The respective displays may be arranged directly above the corresponding charge slot 36 and storage slot 37, and the corresponding stored energy supply for providing information regarding the charged energy supply.

It will be apparent to those skilled in the art that various modifications and variations can be made to the embodiments described herein without departing from the spirit and the scope of the claimed subject matter. Thus it is intended that the specification cover the modifications and variations of the various embodiments described herein provided such modifications and variations come within the scope of the appended claims and their equivalents.

What is claimed is:

1. A medical device comprising an energy supply, the energy supply comprising at least two battery stacks, a control unit and a reservoir, wherein the at least two battery stacks comprise a backup energy source, the control unit monitors and controls the energy supply such that when the control unit detects a fault in the at least two battery stacks, the control unit disconnects a faulty battery stack, and the reservoir is carried by the energy supply, and the reservoir comprises a capacity such that the capacity of the reservoir and the remaining running time of the energy supply are synchronized such that change or refill of the reservoir is required at the same time as a change or recharge of the energy supply.

2. The medical device of claim 1 wherein the energy supply is rechargeable.

3. The medical device of claim 2 wherein the energy supply comprises a lithium-ion polymer battery comprising the at least two battery stacks, and each of the at least two battery stacks comprises a positive potential terminal, a negative potential terminal and one or more battery cells.

4. The medical device of claim 3 wherein each of the at least two battery stacks comprises a cover.

5. The medical device of claim 3 wherein the at least two battery stacks are disposed in one common cover.

6. The medical device of claim 5 wherein the at least two battery stacks are separated by a sealing sheet.

7. The medical device of claim 3 further comprising one common terminal of negative potential connected to the negative potential of each of the at least two battery stacks.

8. The medical device of claim 1 wherein the at least two battery stacks are positioned side-by-side or on top of each other.

9. The medical device of claim 1 wherein the at least two battery stacks are accommodated in an energy supply housing.

10. The medical device of claim 1 wherein the energy supply is replaceable or fixed in the medical device.

11. The medical device of claim 1 wherein the control unit comprises means for measuring and evaluating an output voltage and/or current of each of the at least two battery stacks and means for disconnecting each of the at least two battery stacks.

12. The medical device of claim 11 wherein the control unit comprises a control subunit for each of the at least two battery stacks, such that each control subunit is associated with one of the at least two battery stacks, and comprises the means for measuring and evaluating the output voltage and/or current of an associated battery stack and means for disconnecting the associated battery stack.

13. The medical device of claim 1 wherein each of the at least two battery stacks is provided with a protection circuit that protects from overcharge, over-voltage, under-voltage, or a combination thereof.

14. The medical device of claim 1 wherein the energy supply comprises a fuel gauge unit for estimating a remaining running time of the energy supply.

15. The medical device of claim 1 wherein the energy supply comprises a cavity that accommodates the reservoir and the cavity is formed to accommodate a cylindrically shaped reservoir or a bag.

16. The medical device of claim 15 wherein the reservoir is enclosed by an energy supply housing or the reservoir is carried by the energy supply housing.

17. The medical device of claim 1 wherein at least a part of a housing of the medical device is formed by an energy supply housing.

18. The medical device of claim 1 wherein a contact surface of the energy supply is provided with a gasket.

19. A medical system comprising a medical device comprising an energy supply and a charging station for charging the energy supply wherein the energy supply comprises at least two battery stacks, a control unit and a reservoir, such that the at least two battery stacks comprise a backup energy source, the control unit monitors and controls the energy supply such that when the control unit detects a fault in the at least two battery stacks, the control unit disconnects a faulty battery stack, and the reservoir is carried by the energy supply, and the reservoir comprises a capacity such that the capacity of the reservoir and the remaining running time of the energy supply are synchronized such that change or refill of the reservoir is required at the same time as a recharge of the energy supply, and the charging station comprises an USB-plug, a line connector, a solar cell panel, a primary battery, a plug for a car cigarette lighter outlet, a connector for a mobile phone accumulator, a dynamo, or a combination thereof for supplying energy.

20. The medical system of claim 19 wherein the charging station comprises a storage slot for storing the energy supply such that maintains a desired charge.

* * * * *

UNITED STATES PATENT AND TRADEMARK OFFICE
CERTIFICATE OF CORRECTION

PATENT NO. : 8,403,914 B2
APPLICATION NO. : 12/878071
DATED : March 26, 2013
INVENTOR(S) : Joerg Dogwiler et al.

It is certified that error appears in the above-identified patent and that said Letters Patent is hereby corrected as shown below:

In the Specification

Col. 6, Line 7, "may also combined" should read --may also be combined--;

Col. 8, Lines 2-3, "a battery stack 11 provide" should read --a battery stack 11 provides--; and Col. 9, Lines 4-5, "3.7 Volt" should read --3.7 Volts--.

Signed and Sealed this
Twenty-second Day of October, 2013

Teresa Stanek Rea
*Deputy Director of the United States Patent and Trademark Office*